United States Patent [19]
Howells et al.

[11] 3,976,028
[45] Aug. 24, 1976

[54] AUTOMATIC ARTICLE IMMERSION APPARATUS

[75] Inventors: Francis Thomas Howells, Alresford; John Maldwyn Newman, Andover, both of England

[73] Assignee: Newman-Howells Associates Limited, London, England

[22] Filed: Jan. 17, 1975

[21] Appl. No.: 541,991

[30] Foreign Application Priority Data
Jan. 30, 1974 United Kingdom............... 4307/74

[52] U.S. Cl................................. 118/6; 118/421; 228/425; 134/117
[51] Int. Cl.².......................................... B05C 3/02
[58] Field of Search............... 118/6, 7, 8, 421, 425, 118/423, 429, 426; 266/4 B; 134/84, 85, 61, 117

[56] References Cited
UNITED STATES PATENTS

| | | | |
|---|---|---|---|
| 1,822,385 | 9/1931 | Watson........................... | 118/420 X |
| 2,077,492 | 4/1937 | Ritzert............................ | 118/420 X |
| 2,527,475 | 10/1950 | Toulmin, Jr.................... | 118/420 X |
| 3,165,108 | 1/1965 | Elliott et al..................... | 118/425 X |
| 3,674,040 | 7/1972 | Howells et al.................. | 118/421 |
| 3,807,353 | 4/1974 | Kobernick...................... | 118/425 |

Primary Examiner—Morris Kaplan
Attorney, Agent, or Firm—Berman, Aisenberg & Platt

[57] ABSTRACT

The apparatus comprises a stack of receptacles, side-by-side relationship article holder, receptacle moving means, including a timing device, for automatically moving receptacles out of said stack, and holder moving means, including a timing device, for automatically advancing said holder towards and, after a predetermined time, withdrawing it from a receptacle moved out of the stack whereby an article carried by the holder may be immersed, for a predetermined time, in a fluid carried by said receptacle. In one embodiment a plurality of stacks of receptacles are arranged in side-by-side relationship so as to form a block of said receptacles and the apparatus comprises a movable frame, means for moving said frame from stack to stack of the block of stacks, a vertically movable platform carried by said frame, means for moving said platform vertically so as to bring it into alignment with any receptacle of a stack, means for withdrawing a receptacle, when so aligned, from its stack onto said platform, means movable with said platform and supporting the article holder for vertical movement above and relatively to said platform and means for effecting such vertical movement of the article holder.

14 Claims, 9 Drawing Figures

AUTOMATIC ARTICLE IMMERSION APPARATUS

This invention is for improvements in or relating to automatic article immersion apparatus. The invention is more particularly, but not exclusively concerned with apparatus for the treatment or processing of histological and like specimens. Typical examples of such histological and like specimens are organic tissues and slides bearing exfoliative cytological smears, blood and the like. The processing of such specimens, for medical diagnosis, generally involves the immersion of the specimens serially in a plurality of baths, of different stains, reagents and/or other liquids, for predetermined periods. Originally this work was carried out manually which was both laborious, time consuming and likely to be inaccurate because it depended on a nurse or other person being available to "time" the immersion of the specimens and effect a change-over from one bath to another at the appropriate time.

Apparatus is now available for carrying out such processing or treatment of specimens or the like automatically and an object of the invention is to provide useful improvements in or modifications of such apparatus, particularly as regards the compactness of the apparatus.

According to the present invention there is provided automatic article immersion apparatus comprising a stack of receptacles, an article holder, receptacle moving means, including a timing device, for automatically moving receptacles out of said stack and holder moving means, including a timing device, for automatically advancing said holder towards and, after a predetermined time, withdrawing it from a receptacle moved out of the stack whereby an article carried by the holder may be immersed, for a predetermined time, in a fluid carried by said receptacle.

Conveniently the arrangement is such that the receptacles are moved or extracted out of the block thereof one row after another. In other words all the receptacles on one level in the block of stacks are presented one after the other to the article holder following which all the receptacles on the next level are presented one after the other to the article holder and so on from level to level in the block or assembly of stacks.

Preferably the receptacle extracting means is also adapted automatically, after a predetermined time, to return a receptacle to its position in the stack or block thereof.

Conveniently each receptacle comprises a pallet adapted to support a tank or vessel for a fluid in which an article is to be immersed. Alternatively the receptacle may be a vessel or tank adapted to contain said fluid.

The apparatus may include means for causing agitation between an article in the holder and a fluid in the receptacle in which said article is immersed.

Conveniently the block of receptacles is arranged at the front or back of a substantially rectangular frame or casing, the operating means of the apparatus being positioned in said frame or casing behind said block of receptacles.

The apparatus may also include a tank or receptacle for the draining and/or washing of an article after it has been immersed, means being provided for selecting whether said article should be washed and/or drained.

The invention will be further described, by way of example, with reference to the accompanying drawings and as applied to an apparatus for staining histological specimens. In the drawings.

The disposition of the major elements of the apparatus and their spatial relationship to each other is illustrated in FIGS. 1 – 6 inclusive. It should be noted that the three dimensional Figures give a greatly over-simplified picture of the apparatus and should not be considered as in any way depicting the way in which the machine will necessarily be constructed. Furthermore, in FIGS. 1 to 6 the mechanical elements for imparting the various movements are omitted for the sake of clarity, but are shown in detail in FIGS. 7, 8 and 9.

Figure 1:
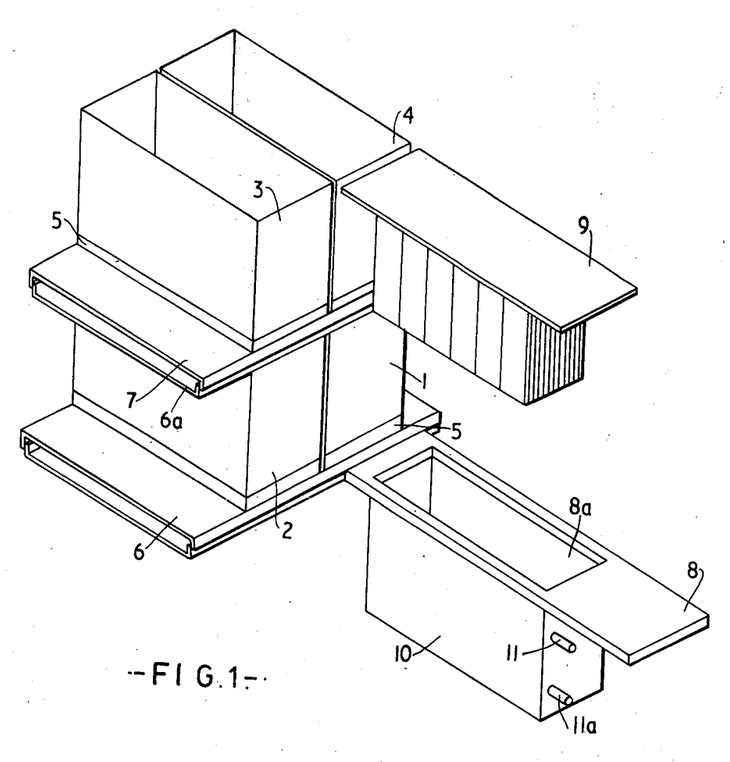
FIGS. 1 to 6 are diagrams illustrating the basic principle on which one particular embodiment of the invention may be put into effect.

In FIG. 1 the reference numerals 1, 2, 3 and 4 indicate tanks for holding the staining solutions. Each tank is mounted on a pallet 5. Two of the tanks (1 and 2) are mounted on a platform 6 and the other two (3 and 4) on a platform 7. Platform 6 will hereinafter be referred to as the first level and platform 7 as the second level.

It will be appreciated that in FIGS. 1 to 6 only four tanks and two platforms are shown for convenience. The apparatus shown in FIGS. 7, 8 and 9 has, in fact, 24 tanks mounted on four platforms in groups of six.

Positioned in front of the tanks is a further platform 8, which is so placed that it lies opposite tank 1 and lies in the same plane as platform 6. Positioned directly over platform 8 is a slide holder 9 which will hold, say, a maximum load of 120, 3 × 1 inch slides suspended vertically. Located below the platform 8 is a wash tank 10 equipped with an inlet 11 and an outlet 11a thus allowing it to be filled from a running water supply. If preferred, it can hold a static supply of water. The platform 8 has an opening 8a in it so that the slides can be immersed in the tank 10. The slide holder is designed to form a closure or cover for a tank when it has been lowered so as to immerse slides therein.

Figure 2:
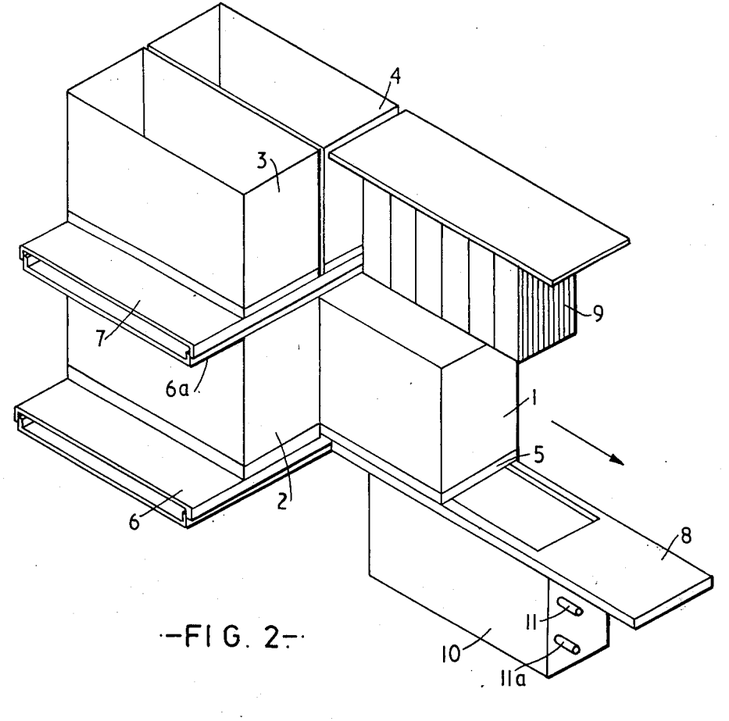
Figure 7:
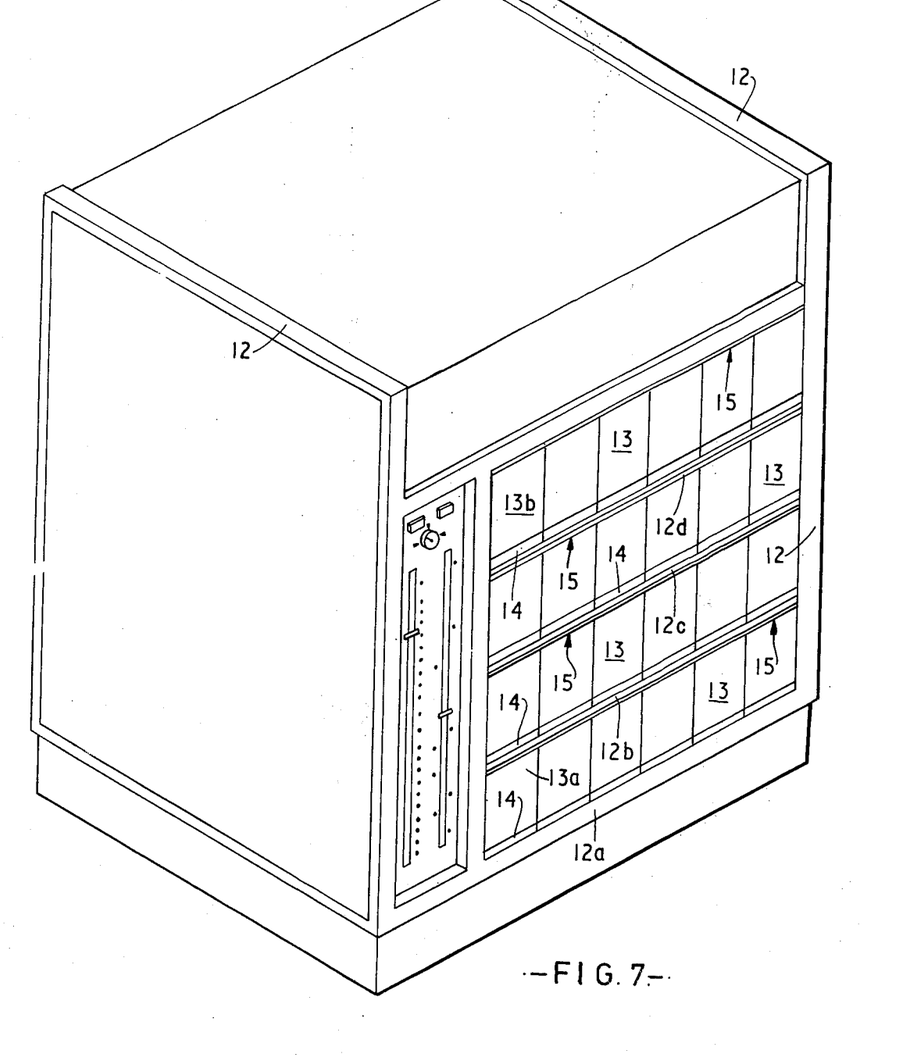
FIG. 7 is a semi-diagrammatic front perspective view of said embodiment of the invention.
Figure 8:
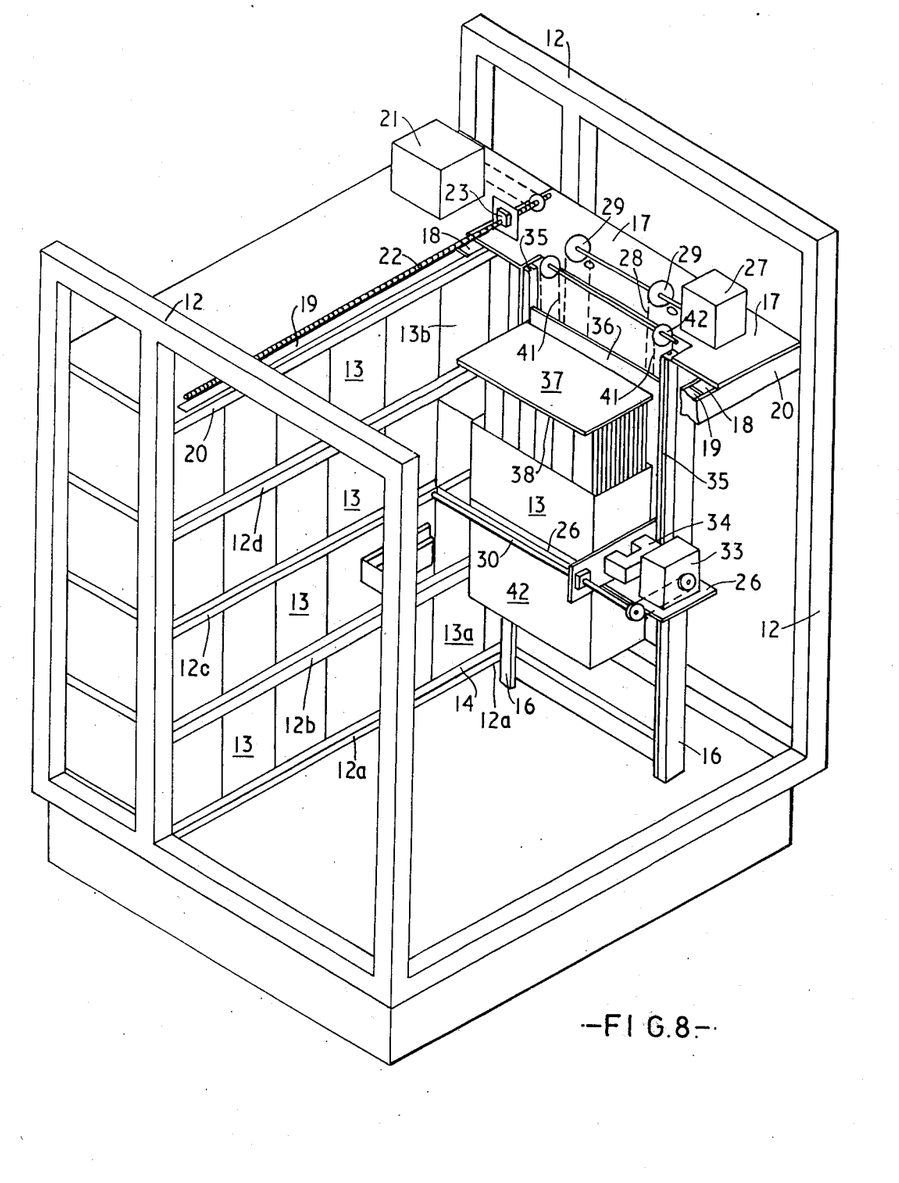
FIGS. 8 and 9 are semi-diagrammatic views of mechanisms incorporated in the apparatus shown in FIG. 7.
Figure 9:
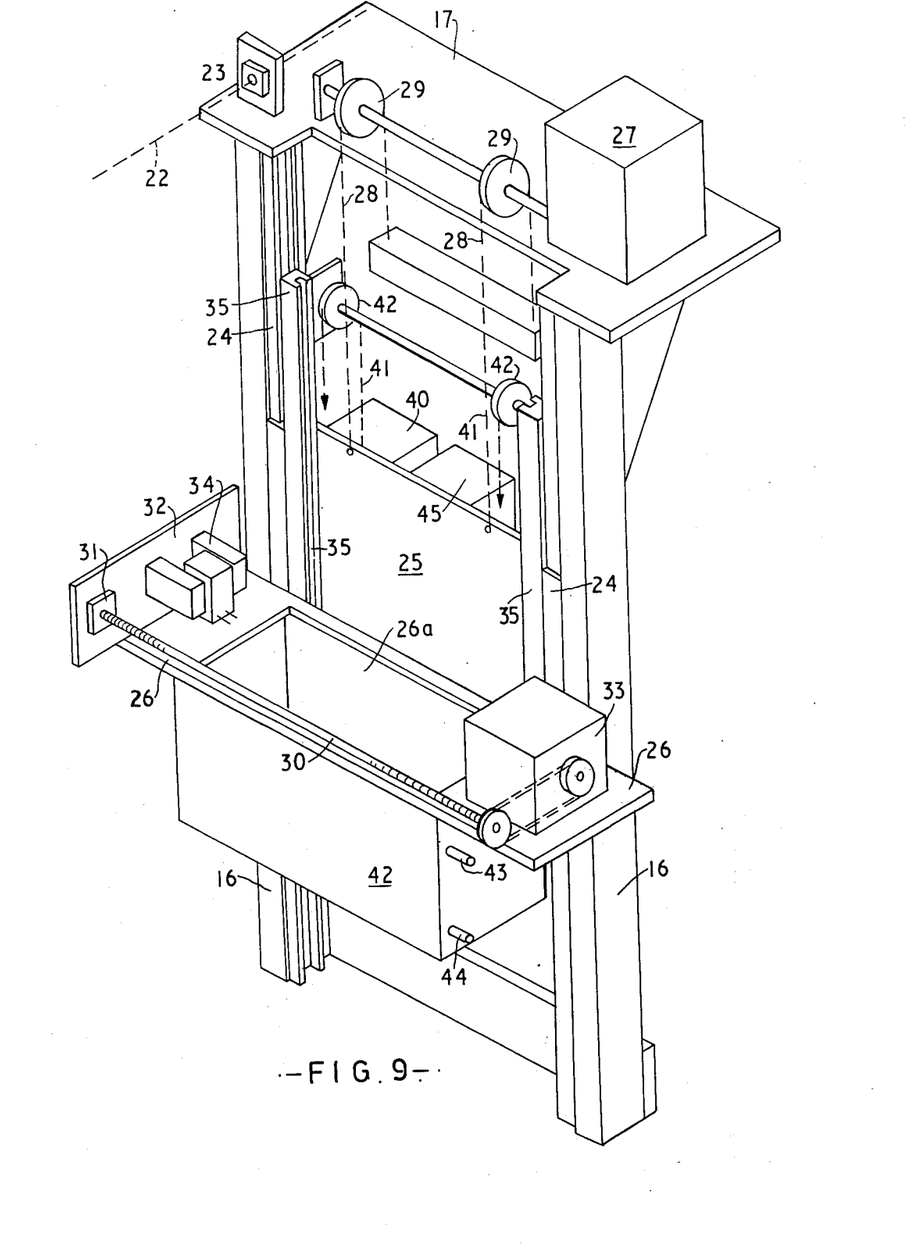

The general relationship of the elements depicted in FIG. 1 can be described as the "normal state" of the apparatus immediately prior to the immersion of the slides in a given stain or water wash or before moving from one tank position to another. FIG. 2 shows tank 1 on its pallet 5 being withdrawn from the platform 6 onto platform 8. It will be noted that none of the other tanks is disturbed and that tank 2 remains covered by the cover 6a, thus preventing any evaporative loss. All 24 of the tanks in the apparatus shown in FIGS. 7, 8 and 9 are protected in a similar manner.

Figure 3:
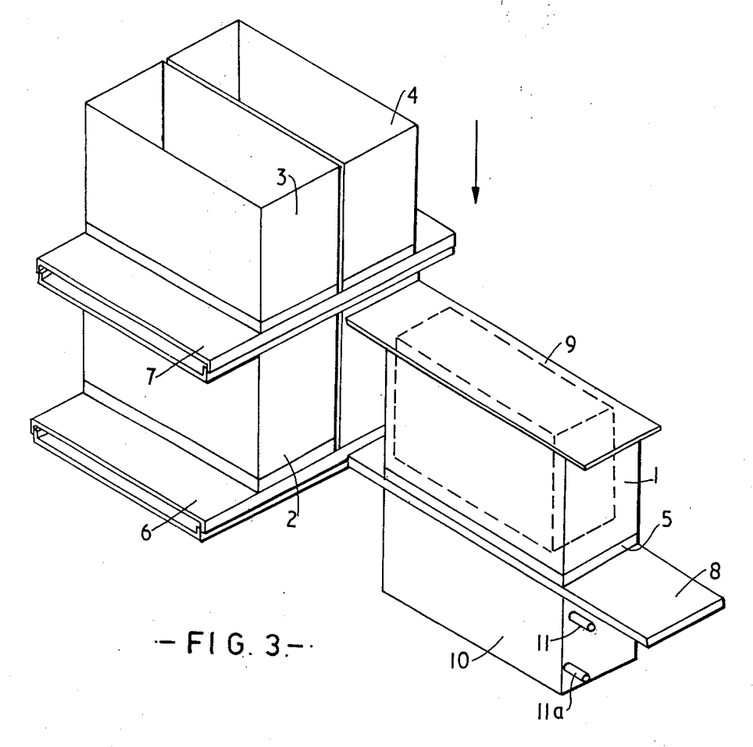

In FIG. 3, the tank 1 is fully withdrawn from the platform 6 and the slide holder 9 has been lowered so that the slides (shown in dotted lines) are immersed in the stain solution in the tank 10. A timing device determines the length of time that the slides remain in the solution. At the end of the required staining time the slide holder is withdrawn to its original position above platform 8 and tank 1 is returned to its original location on platform 6. This restores all elements to the "normal" relationship as illustrated in FIG. 1.

It is a requirement of any modern staining machine that provision be made which allows the slides to either drain off any surplus stain prior to immersion in another stain or, alternatively, that the slides be washed in water (either running or static) before further staining takes place.

Figure 4:
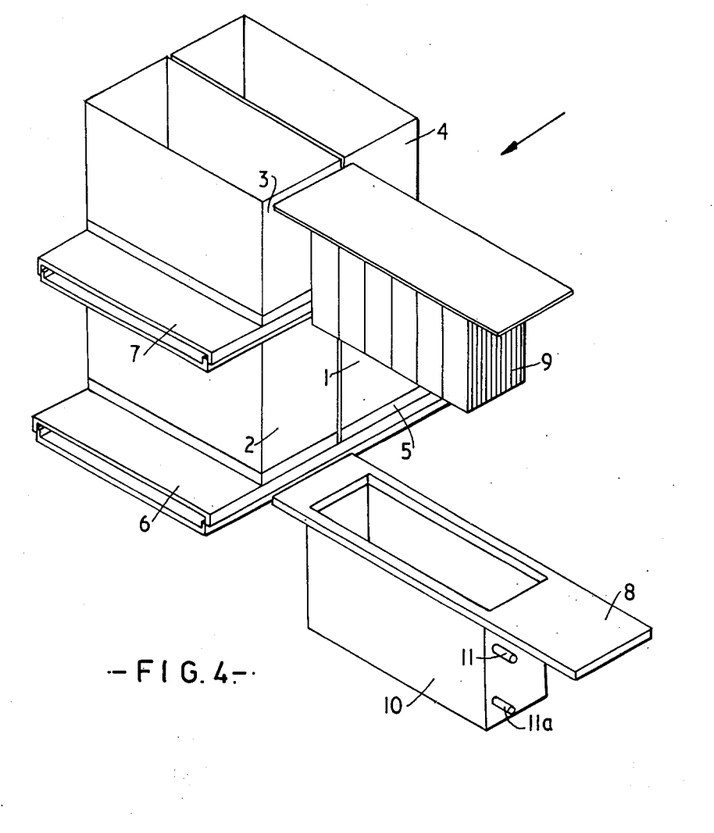

A programming device (not shown) allows the technician to pre-select which mode shall be used. FIG. 4 shows what happens if the drain mode is selected. The slide holder 9 remains in its "normal" raised position above the wash tank 10 into which any surplus stain is drained. At the same time as this is taking place, the platform 8, the slide holder 9 and the tank 10 are moved laterally so that the platform 8 is positioned opposite to tank 2 which contains the next stain to be used in the staining sequence.

Figure 5:
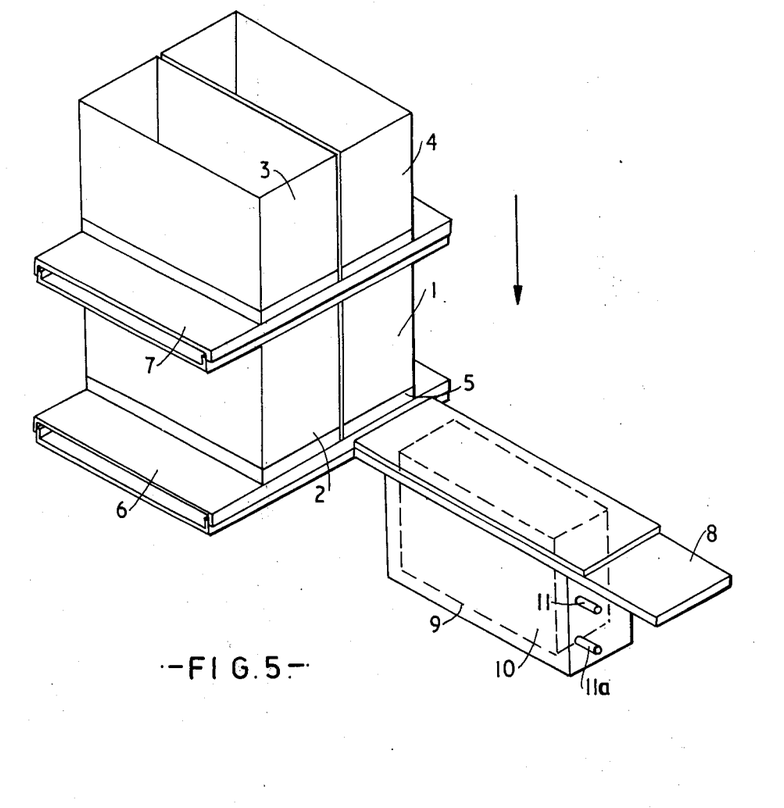

If, however, the washing mode is selected, the slide holder 9 is lowered to the position shown in FIG. 5 allowing the slides to be immersed in the wash tank 10. After washing is completed (timed by a separate timer) the slide holder is raised from tank 10 to its "normal" position above platform 8 and then, in the manner described above, the slide holder 9, the platform 8 and the wash tank 10 are moved laterally so that platform 8 is positioned opposite to tank 2. During this operation any surplus water is drained off into the wash tank 10.

Figure 6:
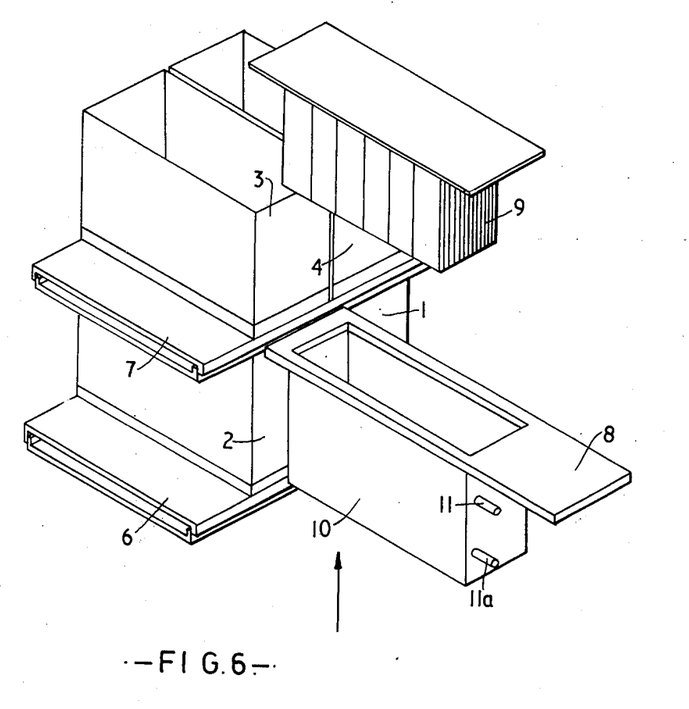

All the operations described above are now repeated with respect to tank 2 and, in the actual machine, (FIGS. 7, 8 and 9) would be repeated until all six tanks on the first level (platform 6) have been utilised. Assuming, for purposes of illustrating the principles involved, that the tank 2 is the last tank on the first level, that it has been returned to its original place on platform 6 and that the slide holder 9 is in its "normal" position, then the platform 8, the slide holder 9 and the wash tank 10 are raised up through such a distance that the platform 8 is positioned level with platform 7 (second level) and opposite tank 3 which holds the next stain to be used in the sequence. This position is shown in FIG. 6.

Tank 3 is withdrawn from platform 7 onto platform 8 and all the operations previously described are repeated. In the actual machine these operations would continue until all the tanks on the second level (platform 7) have been utilized. The platform 8, slide holder 9 and wash tank 10 would then be raised to the third and ultimately the fourth levels. When all 24 tanks have been utilized (or a lesser number if so required) the platform 8, slide holder 9 and wash tank 10 are lowered so that the platform 8 is positioned opposite tank 1 on the first level (platform 6). This tank is adapted so that the slide holder 9 may be detached from the conveying means and is thus returned with tank 1 when the latter is returned from the unloading sequence or station (not shown). Tank 1 may then be removed manually from the machine and the slide holder 9 recovered.

Referring now to FIGS. 7, 8 and 9, the apparatus comprises a tubular metal or like framework 12 which serves to support the elements of the apparatus. At the front of the apparatus there are located platforms 12a, 12b, 12c and 12d located one above the other at first, second, third and fourth levels. Although in preferred embodiments there are four platforms or levels any other convenient number may be used. Located on the said platforms are tanks 13 each of which is mounted on a pallet 14. All the tanks are covered by means of covers 15. The said covers rest on and are supported by all the tanks on any given level and remain so supported should any one tank be removed from a given level. The purpose of the covers is to prevent the evaporation of the fluids from the tanks and also to keep out dust and the like.

Located within the apparatus and positioned vertically and at right-angles to the multiple stack formation of tanks is a frame 16 which is joined at its upper end to a cross-member or platform 17 the outer ends of which are attached to slides or runners 18 adapted to run in horizontal guides 19 positioned parallel to the vertical face of the tank formation and formed by or secured to elements 20 of the main frame 12.

By means of an electric motor drive unit 21 a drive is transmitted to a screw 22 having a nut 23 secured to the cross-member or platform 17. By this screw and nut mechanism and suitable control means the cross-member 17 and the frame 16 can be caused to be moved laterally in either direction along the vertical face of the tank formation and may be positioned or halted at any desired point relative to said tank formation.

Attached to the inner faces of the frame 16 (see FIG. 9) are guides 24 which slidably support a vertically movable frame 25 to which is secured a platform 26 in such a manner that the said platform is at right-angles to said frame. By means of an electric motor drive unit 27 and chains 28 passing over wheels 29 and attached to the frame 25, the platform 26 can be caused to move up and down and by suitable control means be positioned or halted at any of the above-mentioned first, second, third or fourth levels.

Along the free edge of the platform 26 there is positioned a screw 30 having a nut 31 secured to a vertically positioned plate 32. The screw 30 is driven by electric motor drive unit 33 and by suitable control means the plate 32 can be caused, by the screw and nut mechanism 30, 31, to move in either direction along the length of the upper surface of the platform 26. An electro-magnet device 34 is attached to the plate 32.

Attached to the face of the frame 25 are grooved members 35 in which slides a plate 36 (see FIG. 8). Affixed at right-angles to the upper edge of the plate 36 is a further plate 37 which is fitted with means (not shown) for holding a slide carrier 38. The grooved members 35 extend a certain distance above the upper edge of the frame 25 so that the plate 36 can be raised upwards to a certain height relative to the upper surface of the platform 26. This is accomplished by means of an electric motor drive unit 40 mounted on the rear face of the frame 25, the drive from which is engaged with chains 41 which pass over wheels 42, supported from the upper ends of the grooved members 35, and are attached to the upper edge of the plate 36. By suitable control means the plate 36 may be raised or lowered and positioned or halted in any desired position relative to the platform 26 and to a washing tank 42 positioned below the platform 26 and moving with it at all times. The tank 42 is equipped with means 43 for filling it with water or other liquid and with means 44 for emptying it.

Also attached to the rear face of the frame 25 is a further electric motor drive unit 45 which imparts an oscillating or reciprocating motion to the chains 41 and thus to the plate 36 whereby the said plate is caused to be moved up and down through a sort distance. As a result the plate 37, which is attached to plate 36, and the slide holder 38 are moved or reciprocated through a like distance. This motion is for agitating the slides or specimens when immersed in one of the tanks.

The apparatus above described is operated as follows. The slides having been loaded into the slide carrier 38, the said carrier is loaded into a loading/unloading tank 13a which is placed on its pallet 14 in the preferred place in the line of tanks on the first level, i.e., on platform 12a. For the purpose of loading the slide carrier 38 onto its conveying means within the apparatus, the frame 16 and the platform 26 together with the plate 37 and the means for carrying the slide holder 38, are positioned so that the platform 26 is located opposite the loading/unloading tank 13a and level with platform 12a.

By suitable control means, the electro-magnet 34 is energized and the magnetized pole pieces attract and engage with a metal strip attached to the face of the pallet 14. Supporting the loading/unloading tank 13a. The motor drive unit 33 is now energized and drives the screw 30 which being engaged with the nut 31 secured to the plate 32, causes said plate to move along the length of platform 26, the electro-magnet drawing or extracting the pallet together with the loading/unloading tank 13a onto the platform 26. In so doing, the means (i.e. the plate 37) for holding the slide carrier 38 automatically engages with a part of the said slide carrier. Thus, the slide carrier is attached to the plate 37. The motor drive unit 40 is now energized and the plate 36 together with the plate 37, and the slide holder 38 are raised by the chains 41 through a sufficient distance so that the base of the slide holder 38 is clear of the upper edge of the tank 13a by a sufficient distance which would allow the said tank to be returned to its original location on platform 12a. This action is carried out by suitable control means reversing the drive motor unit 33 so that the plate 32 is caused to travel in the opposite direction. When travelling in this direction, the electro-magnet 34 may or may not be energized.

It is a requirement of the staining art that provision be made which allows the slides or the like to drain off any surplus stain before applying a further stain, or alternatively, that the slides or the like be washed in running water or in a vessel containing a static water supply, again before applying any further stain. Programming means are provided whereby the operator of the apparatus can decide prior to the commencement of the staining cycle which action shall take place between immersion of the slides or the like in successive stains, the programming device being such that any combination of draining or washing is possible.

Assuming that the draining mode has been selected, the motor drive unit 21 is energized causing the screw 22, which is engaged with the nut 23 affixed to the cross-member or platform 17, to move the latter the frame 16, the platform 26, the plate 36 and the slide holder 38 laterally through a distance so that the platform 26 is positioned opposite the next adjacent tank 13 in the staining sequence. During this movement, the slide carrier 38 remains in the raised position allowing any surplus stain to be drained into the wash tank 42 positioned below the platform 26 and moving with it.

Alternatively, if the washing mode is selected, the motor drive unit 40 is energized causing the plate 36 and the slide holder 38 to be lowered so that the holder passes through the aperture 26a in the platform 26 and immersing the slides or the like in the water or other liquid. Separate timing means previously programmed by the operator determines the length of time that the slides are washed. On completion of the wash, the motor drive unit 40 is energized and plate 36 and the slide holder 38 are raised upwards as described heretofore. The motor drive unit 21 is then energized causing the frame 16, the platform 26, the plate 36 and the slide holder 38 to move laterally through a distance such that platform 26 is positioned opposite the next adjacent tank 13 in the staining sequence. The drainage of any water from the slides takes place during this movement and any surplus water is drained back into the wash tank 42.

The operations previously described are repeated until all the tanks on the first level platform 12a have been utilized and have been returned to their original positions. The motor drive unit 27 is then energized to cause the chains 28, running over the wheels 29, to lift the frame 25 together with the platform 26, the plate 36 and plate 37, the slide holder 38 and the wash tank 42 through such a distance that the platform 26 is positioned level with the second level platform 12b and the next tank 13 in the staining sequence.

All the operations previously described in respect of the immersion of the slide holder and slides or the like in the plurality of tanks on the first level platform 12a and/or the draining or washing of the said slides or the like, are repeated for all tanks on the second level platform 12b and subsequently for the third level platform 12c and the fourth level platform 12d. When the last tank, characterised in this instance by the reference numeral 13b, on the fourth level platform 12d, but which could be any of the total plurality of tanks, has been utilized, programming means energizes the motor drive unit 27 to cause the platform 26, the plate 36 and the slide holder 38 to be lowered to a point where the platform 26 is again positioned opposite to the loading-/unloading tank 13a and level with platform 12a. The electro-magnet 34 is then energized and engages with the pallet 14 supporting the loading/unloading tank 13a which is then conveyed in the manner described heretofore until the tank 13a is positioned on platform 26 immediately below the slide holder 38. The motor drive unit 40 is then energized and the slide holder 38 lowered into tank 13a. Motor drive unit 33 is then energized and conveys the tank 13a on its pallet 14 to its original position on the first level platform 12a. In performing this action, the slide holder 38 is disengaged from its carrying means secured to the plate 37. The electro-magnet 34 is then de-energised and the tank 13a on its pallet 14 can then be manually removed from platform 12a and the slide holder 38 from the said tank.

The electric circuitry of the apparatus will include, in addition to the several electric motors and the electromagnet, previously described, electric timers, programming means, switches and other devices necessary for the apparatus to carry out the required sequence of operation automatically. The programming means, which may be of known form, will be designed to provide for the selection of various different sequences of operation and for changes in such sequences and operations as and when required.

Although the invention has been described more particularly as applied to the processing of histological and like specimens it has a much wider field of application where processing by immersion in a series of fluids is involved. For example, apparatus according to the invention could be used with advantage in the electroplating or coating of metals and other materials.

We claim:

1. Automatic article immersion apparatus comprising a stationary stack of receptacles; an article holder; receptacle extraction means, including a timing device, for automatically moving receptacles out of said stack; holder moving means, including a timing device, for automatically advancing said holder towards and, after a predetermined time, withdrawing it from a receptacle moved out of the stack whereby an article carried by the holder may be immersed, for a predetermined time in a fluid carried by said receptacle; and means for moving the receptacle extraction means to register with, and be operative for withdrawing, desired receptacles in turn.

2. Automatic article immersion apparatus comprising a plurality of stacks of receptacles arranged in side-by-side relationship so as to form a stationary block of said receptacles; an article holder; receptacle extraction means, including a timing device, for automatically moving receptacles out of said block of receptacles; holder moving means, including a timing device, for automatically advancing said holder towards and, after predetermined time, withdrawing it from a receptacle moved out of the block whereby an article carried by the holder may be immersed for a predetermined time, in a fluid carried by said receptacle; and means for moving the receptacle extraction means to register with, and be operative for withdrawing, desired receptacles in turn.

3. Apparatus as claimed in claim 2 wherein said receptacle extraction means comprises; a movable frame, means for moving said frame from stack to stack of the block of stacks, a vertically movable platform carried by said frame, means for moving said platform vertically so as to bring it into alignment with any receptacle of a stack, and means for withdrawing a receptacle, when so aligned from its stack onto said platform; said holder moving means being movable with said platform and supporting the article holder for vertical movement above and relative to said platform and including means for effecting such vertical movement of the article holder.

4. Apparatus as claimed in claim 2, wherein the block of receptacles is arranged at one side of a substantially rectangular frame or casing, the receptacle extraction means and holder moving means being positioned in said frame or casing behind said block of receptacles.

5. Apparatus as claimed in claim 2 wherein each receptacle comprises a pallet adapted to support a tank or vessel for a fluid in which an article is to be immersed.

6. Apparatus as claimed in claim 2 wherein the receptacle extraction means is adapted automatically, after a predetermined time, to return a receptacle to its position in a stack.

7. Apparatus as claimed in claim 2 wherein the receptacles are moved out of the block thereof one row after another.

8. Apparatus as claimed in claim 2 and including a receptacle for the washing of an article or for the drawing off of fluid from an article which has been immersed and means for selecting whether said article should be washed or drained.

9. Apparatus as claimed in claim 2 and including cover means for the receptacles.

10. Apparatus as claimed in claim 3 wherein the extraction means for withdrawing a receptacle from the block includes a magnet device for temporarily attaching a receptacle to said means.

11. Apparatus as claimed in claim 3 wherein a vessel for the washing and draining of an article, which has been immersed, is carried by said platform below an opening therein.

12. Apparatus as claimed in claim 2 and including means for causing agitation between an article in the holder and a fluid in the receptacle in which said article is immersed.

13. Apparatus as claimed in claim 3 wherein means is provided for imparting an oscillating or reciprocating motion to the means supporting the article holder thereto to agitate an article in the holder.

14. Apparatus as claimed in claim 2 wherein the article holder is provided with means for automatically engaging an article carrier when presented to it by movement of a receptacle, carrying said article carrier, out of its stack.

* * * * *